United States Patent
Yuan (10) Patent No.: US 11,441,889 B2
(45) Date of Patent: Sep. 13, 2022

(54) APPARATUS, SYSTEMS, AND METHODS FOR DETECTING LIGHT

(71) Applicant: Nokia Technologies Oy, Espoo (FI)

(72) Inventor: Xin Yuan, New Providence, NJ (US)

(73) Assignee: NOKIA TECHNOLOGIES OY, Espoo (FI)

( * ) Notice: Subject to any disclaimer, the term of this patent is extended or adjusted under 35 U.S.C. 154(b) by 105 days.

(21) Appl. No.: 16/757,720

(22) PCT Filed: Oct. 19, 2018

(86) PCT No.: PCT/FI2018/050766
§ 371 (c)(1),
(2) Date: Apr. 20, 2020

(87) PCT Pub. No.: WO2019/081807
PCT Pub. Date: May 2, 2019

(65) Prior Publication Data
US 2021/0372767 A1    Dec. 2, 2021

(30) Foreign Application Priority Data

Oct. 27, 2017  (EP) ..................................... 17199046

(51) Int. Cl.
*G01B 9/02091* (2022.01)
*A61B 5/00* (2006.01)
(Continued)

(52) U.S. Cl.
CPC ........ *G01B 9/02091* (2013.01); *A61B 5/0066* (2013.01); *A61B 5/0073* (2013.01);
(Continued)

(58) Field of Classification Search
CPC ............ G01B 9/02091; G01B 9/02002; G01B 9/02041; G01B 9/02044; G01B 9/02087;
(Continued)

(56) References Cited

U.S. PATENT DOCUMENTS

| 5,418,380 A | 5/1995 | Simon et al. |
| 9,429,516 B2 | 8/2016 | Choi et al. |

(Continued)

FOREIGN PATENT DOCUMENTS

| CN | 101228460 A | 7/2008 |
| CN | 201328803 Y | 10/2009 |

(Continued)

OTHER PUBLICATIONS

Office Action for European Application No. 17199046.8 dated May 20, 2021, 5 pages.

(Continued)

*Primary Examiner* — Dominic J Bologna
(74) *Attorney, Agent, or Firm* — Alston & Bird LLP (57) ABSTRACT

Described herein are an apparatus, system, and method for detecting light. An apparatus can include means for modulating an input beam of light wherein the input beam of light is obtained from an optical coherence tomography arrangement; means for dispersing the modulated beam of light; and means for detecting the dispersed beam of light and converting the detected beam of light into an electrical output signal. An apparatus can include a modulator configured to spatially modulate light; a dispersing element configured to disperse modulated light, and a detector configured to detect dispersed light and convert the detected light into electrical output signals. A method can include spatially modulating a beam of light, dispersing the modulated beam of light, detecting the dispersed beam of light, converting the detecting beam of light into electrical output signals, and providing a three-dimensional image of at least a part of an object.

22 Claims, 5 Drawing Sheets

(51) Int. Cl.
| | |
|---|---|
| *G01B 9/02002* | (2022.01) |
| *G01B 9/02* | (2022.01) |
| *G01J 3/02* | (2006.01) |
| *G01J 3/28* | (2006.01) |
| *A61B 3/12* | (2006.01) |

(52) U.S. Cl.
CPC ..... *G01B 9/02002* (2013.01); *G01B 9/02041* (2013.01); *G01B 9/02044* (2013.01); *G01B 9/02087* (2013.01); *G01J 3/0229* (2013.01); *G01J 3/2803* (2013.01); *G01J 3/2823* (2013.01); *G01J 3/2846* (2013.01); *A61B 3/1225* (2013.01)

(58) Field of Classification Search
CPC ... A61B 5/0066; A61B 5/0073; A61B 3/1225; G01J 3/0229; G01J 3/2803; G01J 3/2823; G01J 3/2846
See application file for complete search history.

(56) References Cited

U.S. PATENT DOCUMENTS

| | | | |
|---|---|---|---|
| 2006/0274308 A1 | 12/2006 | Brady et al. | |
| 2007/0097363 A1* | 5/2007 | Brady | G01J 3/0229 356/310 |
| 2007/0165223 A1 | 7/2007 | Wilson et al. | |
| 2007/0182962 A1* | 8/2007 | Bearman | G01J 3/2803 356/328 |
| 2008/0304074 A1 | 12/2008 | Brennan, III | |
| 2009/0095912 A1 | 4/2009 | Slinger et al. | |
| 2011/0285995 A1 | 11/2011 | Tkaczyk et al. | |
| 2014/0146324 A1 | 5/2014 | Lim et al. | |
| 2016/0235482 A1* | 8/2016 | Wood | A61B 90/37 |
| 2017/0003168 A1* | 1/2017 | Fujii | G01J 3/2823 |
| 2017/0255104 A1 | 9/2017 | Polo et al. | |
| 2019/0162596 A1 | 5/2019 | Fujii et al. | |

FOREIGN PATENT DOCUMENTS

| | | |
|---|---|---|
| CN | 102499648 A | 6/2012 |
| CN | 103829924 A | 6/2014 |
| JP | 2008157710 A | 7/2008 |
| JP | 2010-529465 A | 8/2010 |
| JP | 2017-015694 A | 1/2017 |
| WO | WO 2014/193310 A1 | 12/2014 |

OTHER PUBLICATIONS

Office Action for Japanese Application No. 2020-523404 dated Jun. 4, 2021, 8 pages.

Onuma, K., "Illustrated Swept Source OCT Measurement Principle and Clinical Application", Japanese Journal of Visual Science, vol. 34, Issue 1, (2013), pp. 20-26.

Office Action for Chinese Application No. 201880069959.7 dated May 17, 2021, 18 pages.

Dubois, A. et al., *High-Resolution Full-Field Optical Coherence Tomography With a Linnik Microscope*, Applied Optics, vol. 41, No. 4 (Feb. 2002) 805-812.

Fercher, A. F. et al., *Optical Coherence Tomography—Principles and Applications*, Rep. Prog. Phys. 66 (2003) 239-303.

Huang, D. et al., *Optical Coherence Tomography*, Science (Nov. 1991) 1178-1181, 12 pages.

Kittle, D. et al., *Multiframe Image Estimation for Coded Aperture Snapshot Spectral Imagers*, Applied Optics, vol. 49, No. 36 (Dec. 2010) 6824-6833.

Liu, X. et al., *Compressive SD-OCT: The Application of Compressed Sensing in Spectral Domain Optical Coherence Tomography*, Optics Express, vol. 18, No. 21 (Oct. 2010) 22010-22019.

Llull, P. et al., *Coded Aperture Compressive Temporal Imaging*, Optics Express, vol. 21, No. 9 (May 2013) 20 pages.

Lustig, M. et al., *Compressed Sensing MRI*, IEEE Signal Processing Magazine (Mar. 2008) 72-82.

Lustig, M. et al., *Sparse MRI: The Application of Compressing Sensing for Rapid MR Imaging*, Magnetic Resonance in Medicine 58 (2007) 1182-1195.

Wagadarikar, A. et al., *Single Disperser Design for Coded Aperture Snapshot Spectral Imaging*, Applied Optics, vol. 47, No. 10 (Apr. 1, 2008) B44-B51.

Yuan, X. et al., *Compressive Hyperspectral Imaging With Side Information*, IEEE Journal of Selected Topics in Signal Processing, vol. 9, No. 6 (Sep. 2015) 964-976.

Yuan, X. et al., *Low-Cost Compressive Sensing for Color Video and Depth*, 2014 IEEE Conference on Computer Vision and Pattern Recognition, (2014) 3318-3325.

Zysk, A. M. et al., *Optical Coherence Tomography: A Review of Clinical Development From Bench to Bedside*, Journal of Biomedical Optics 12(5) (Sep./Oct. 2007) 21 pages.

International Search Report and Written Opinion for Application No. PCT/FI2018/050766 dated Nov. 29, 2018, 14 pages.

Extended European Search Report for Application No. EP 17199046.8 dated Mar. 15, 2018, 12 pages.

\* cited by examiner

APPARATUS, SYSTEMS, AND METHODS FOR DETECTING LIGHT

CROSS-REFERENCE TO RELATED APPLICATIONS

This Application is a National Stage Entry of International Patent Application No. PCT/FI2018/050766, filed Oct. 19, 2018, entitled "Apparatus, Systems and Methods for Detecting Light," which claims priority to and the benefit of European Patent Application No. 17199046.8, filed Oct. 27, 2017, entitled "Apparatus, Systems and Methods for Detecting Light," the entire disclosures of each of which are hereby incorporated herein by reference in their entireties for all purposes.

TECHNOLOGICAL FIELD

Examples of the disclosure relate to apparatus, systems and methods for detecting light. In particular they relate to apparatus, systems and methods for detecting light from an optical coherence tomography arrangement.

BACKGROUND

Optical coherence tomography enables cross sectional imaging of an object such as a retina by detecting the light reflected from internal structures within the object.

It is useful to provide means for detecting the light from optical coherence tomography arrangements which enable a high quality image to be obtained.

BRIEF SUMMARY

According to various, but not necessarily all, embodiments of the invention there is provided an apparatus comprising: means for modulating an input beam of light wherein the input beam of light is obtained from an optical coherence tomography arrangement; means for dispersing the modulated beam of light; and means for detecting the dispersed beam of light and converting the detected beam of light into an electrical output signal.

In some but not necessarily all examples, the means for modulating the input beam of light comprises a coded aperture. The coded aperture is, in some but not necessarily all examples, a two dimensional coded aperture.

In some but not necessarily all examples, the means for modulating the input beam of light comprises at least a first portion having a first transparency to the input beam of light and at least a second portion having a different transparency to the input beam of light. The transparency of the portions of the means for modulating the input beam of light are, in some but not necessarily all examples, wavelength dependent.

The portions of the means for modulating the input beam of light having different transparencies are, in some but not necessarily all examples, arranged in a random pattern.

In some but not necessarily all examples, the means for modulating the input beam of light is arranged to convert a three dimensional signal into a two dimensional signal.

In some but not necessarily all examples, the means for modulating the input beam of light is arranged to be moveable relative to the means for dispersing the modulated beam of light and means for detecting the dispersed beam of light.

In some but not necessarily all examples, the means for dispersing the modulated beam of light comprises at least one of; a prism, a grating.

In some but not necessarily all examples, the means for detecting the dispersed beam of light comprises at least one of a: charge coupled device, and a complementary metal-oxide semiconductor sensor.

In some but not necessarily all examples, the means for detecting the dispersed beam of light comprises a two dimensional array of sensors.

In some but not necessarily all examples, the optical coherence tomography arrangement is arranged so that the input beam of light comprises different frequencies of light and the different frequencies of light provide information about different depths within the object.

According to various, but not necessarily all, embodiments of the invention there is provided a sensing system comprising:
  a plurality of apparatus where the plurality of apparatus comprise means for modulating an input beam of light wherein the input beam of light is obtained from an optical coherence tomography arrangement; means for dispersing the modulated beam of light; and means for detecting the dispersed beam of light and converting the detected beam of light into an electrical output signal; and
  one or more filters arranged to divide the input beam of light into a plurality of different bandwidths wherein the sensing system is arranged so that different bandwidths are provided to different apparatus.

In some but not necessarily all examples, the sensing system is arranged so that the different apparatus within the system detect the different dispersed beams of light simultaneously.

According to various, but not necessarily all, embodiments of the invention there is provided a method comprising:
  modulating an input beam of light wherein the input beam of light is obtained from an optical coherence tomography arrangement;
  dispersing the modulated beam of light; and
  detecting the dispersed beam of light and converting the detected beam of light into an electrical output signal.

In some but not necessarily all examples, the method comprises using a coded aperture to modulate the beam of light and moving the coded aperture so that different bandwidths are detected sequentially.

According to various, but not necessarily all, embodiments of the invention there is provided an apparatus comprising:
a modulator arranged to modulate an input beam of light wherein the input beam of light is obtained from an optical coherence tomography arrangement;
at least one dispersing element arranged to disperse the modulated beam of light; and
a detector arranged to detect the dispersed beam of light and convert the detected beam of light into an electrical output signal.

According to various, but not necessarily all, embodiments of the invention there is provided examples as claimed in the appended claims.

BRIEF DESCRIPTION OF THE DRAWINGS

For a better understanding of various examples that are useful for understanding the detailed description, reference will now be made by way of example only to the accompanying drawings in which.

DETAILED DESCRIPTION

Examples of the disclosure relate to an apparatus 1 which can be used as a detector for an optical coherence tomography (OCT) arrangement 17. The apparatus 1 provides for compressed sampling of the input beam of light and disperses different bandwidths of the beam of light. This enables a low cost detector such as a charge-coupled device (CCD) to be used within the apparatus to detect the beams of light.

Figure 1:
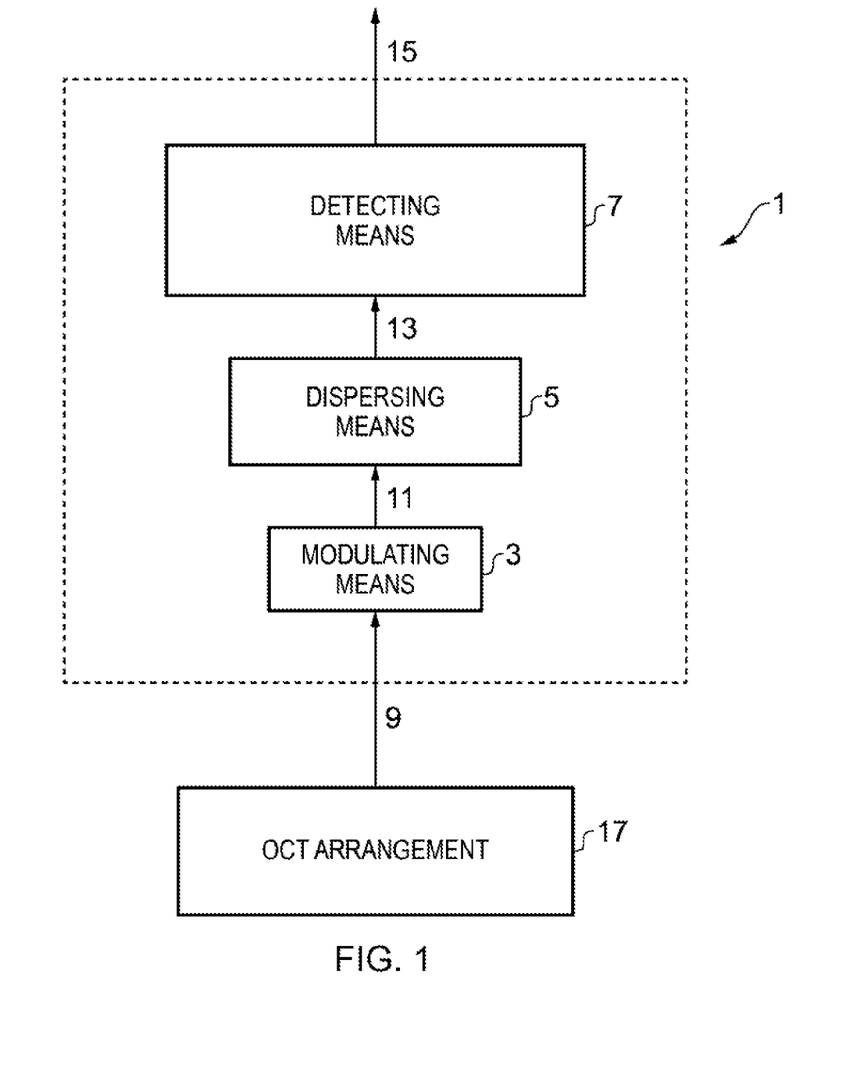
FIG. 1 illustrates an example apparatus.

FIG. 1 schematically illustrates an example apparatus 1. The example apparatus 1 comprises means 3 for modulating an input beam of light 9 wherein the input beam of light 9 is obtained from an optical coherence tomography arrangement 17; means 5 for dispersing the modulated beam of light 11; and means 7 for detecting the dispersed beam of light 13 and converting the detected beam of light into an electrical output signal 15.

The means 3 for modulating the input beam of light 9 comprises a modulator. The modulator 3 is arranged within the apparatus 1 so that when the apparatus 1 is coupled to an OCT arrangement 17, an input beam of light 13 from the OCT arrangement 17 is incident, at least in part, upon the modulator 3.

The modulator 3 enables compressed sampling of the input beam of light 9. The modulator 3 may selectively remove information from the input beam of light 9 so that only portions of the input beam of light 9 is detected. In some examples the modulator 3 may be arranged to convert a three dimensional signal into a two dimensional signal.

The modulator 3 may comprise any means which may be arranged to spatially modulate the input beam of light 9. In some examples the modulator 3 comprises a coded aperture. The coded aperture may comprise an optical mask or any other suitable type of aperture. The coded aperture may be a two dimensional coded aperture or any other suitable type of aperture. In other examples the modulator 3 could comprise a liquid crystal on silicon (LCOS) modulator, or any other suitable type of modulator 3.

In some examples the modulator 3 may comprise at least a first portion having a first level of absorbency to the input beam of light 9 and at least a second portion having a second, different level of absorbency to the input beam of light 9. The different levels of absorbency may allow different levels of light to pass through the modulator 3. It is to be appreciated that the modulator 3 may comprise a plurality of first portions and a plurality of second portions. In some examples the modulator 3 may be a binary modulator 3 so that only two different absorbencies are provided by the respective portions of the modulator 3. In other examples the modulator 3 may be a grey-scale aperture and may comprise more than two different levels of absorbency in the different portions of the modulator 3.

In some examples the absorbency of the portions of the modulator 3 may be wavelength dependent. In such examples the modulation of the input beam of light 9 by the respective portions of the modulator 3 will be dependent upon the wavelengths within the input beam of light 9.

The different portions of the modulator 3 may be arranged in any suitable pattern. In some examples the respective portions of the modulator 3 having different absorbencies are arranged in a pixelated arrangement. The pixelated arrangement may comprise the respective portions of the modulator 3 being arranged in an array of columns and rows. The rows and columns may correspond to the pixels in the detector 7. The number of absorbent pixels, partially absorbent pixels, and non-absorbent pixels may vary in different implementations of the disclosure. In some examples approximately half of the pixels could be absorbent so that half of the incident area of the modulator acts to block the input beam of light 9 while the other half allows the incident beam of light to pass, or partially pass through.

In some examples the different portions of the modulator 3 may be arranged in a random pattern. The random pattern may be an irregular pattern. The random pattern might not be defined or arranged in relation to any specific object. In some examples the different portions of the modulator 3 may be arranged in a pseudo random pattern. In other examples the respective portions of the modulator 3 may be arranged in a predetermined pattern. The predetermined pattern may be selected according to the object or type of object that is to be imaged by the OCT system.

In some examples the modulator 3 may be fixed in position relative to the other components of the apparatus 1. In other examples the modulator 3 may be arranged to be moveable relative to the other components of the apparatus 1. In particular the modulator 3 may be moveable so that the modulator 3 can be shifted relative to the means 5 for dispersing the modulated beam of light 11 and the means 7 for detecting the dispersed beam of light 13.

The modulator 3 provides a modulated beam of light 11 as an output. The means 5 for dispersing the modulated beam of light 11 is arranged within the apparatus 1 so that the modulated beam of light 11, or at least part of the modulated beam of light 11, provided by the modulator 3 is incident upon the means 5 for dispersing the modulated beam of light 11.

The means 5 for dispersing the modulated beam of light 11 may comprise one or more dispersing elements. The dispersing elements 5 may comprise any elements which cause different wavelengths of the modulated beam of light 11 to be refracted by different amounts. The one or more dispersing elements 5 may comprise a prism, a grating or any other suitable elements.

The dispersing elements 5 provide a dispersed beam of light 13 as an output. The means 7 for detecting the dispersed beam of light 13 is arranged within the apparatus 1 so that the dispersed beam of light 13, or at least part of the dispersed beam of light 13, is incident on the means 7 for detecting the dispersed beam of light 13.

The means 7 for detecting the dispersed beam of light 13 comprises a detector 7. The detector 7 may be arranged to transduce an incident beam of light into an electrical output signal. In some examples the detector 7 may comprise a charge-coupled device, complementary metal-oxide semiconductor (CMOS) sensors or any other suitable type of sensors.

In some examples the detector 7 may comprise a two dimensional array of sensors. In other examples the detector 7 may comprise a linear detector which may be scanned across a detecting plane.

The output signal 15 provided by the detector 7 therefore comprises information indicative of the object imaged by the OCT arrangement 17. This image may be rendered on a display or other suitable user output device.

Figure 2:
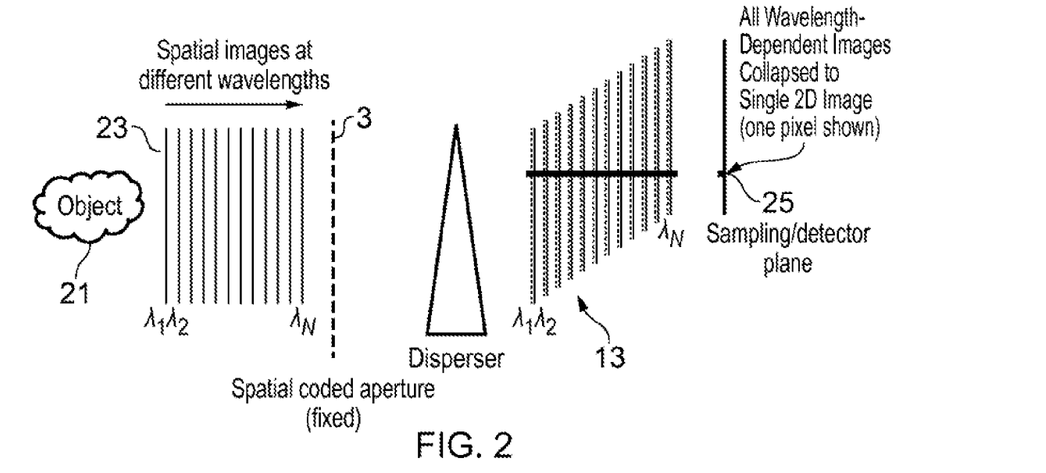
FIG. 2 illustrates an imaging principle.

FIG. 2 shows an imaging principle of examples of the disclosure.

In the example of FIG. 2 an OCT arrangement (not shown for clarity) is used to image an object 21. The object 21 reflects light which has been directed onto the object 21. Different wavelengths of the incident light are reflected differently depending upon the internal structure of the object 21. This provides a plurality of spatial images 23. Each of the spatial images 23 corresponds to a different wavelength of light $\lambda_1$ to $\lambda_n$. The different spatial images 23 therefore comprise information about the internal structure of the object 21. The different spatial images 23 may comprise a three dimensional signal.

In the example of FIG. 2 the modulator 3 comprises a two dimensional coded aperture. Other types of modulator 3 may be used in other examples of the disclosure. In the example of FIG. 2 the modulator 3 is fixed in position relative to the disperser 5 and the detector 7. In other examples the modulator 3 could be moveable relative to the disperser 5 and the detector 7 and any other suitable components of the apparatus 1.

The spatial images 23 in the input beam of light 9 are modulated by the coded aperture. The coded aperture blocks and/or at least partially blocks portions of each of the different spatial images 23. The coded aperture may be wavelength dependent so that different spatial images 23 corresponding to different wavelengths may be blocked by different amounts.

The modulated beam of light 11 provided by the modulator 3 is then spread by the dispersing element 5. In the example of FIG. 2 the dispersing element 5 comprises a prism. Other types of dispersing element 5 could be used in other examples of the disclosure. The dispersing element 5 refracts the modulated beam of light 11 to spatially spread the modulated beam of light. Different bandwidths of the spatial images 23 are spread by a different amount as shown schematically in FIG. 2. The distance by which a spatial image 23 is spread by the dispersing element 5 is dependent upon the wavelength of the spatial image 23.

The dispersed beam of light 13 is then incident upon the detector 7. The detector 7 comprises a plurality of pixels 25. Only one pixel 25 is shown for clarity in FIG. 2. The plurality of pixels 25 may be arranged in any suitable array. In the example of FIG. 2 the plurality of pixels 25 may be arranged in a matrix array comprising i rows and j columns. Each pixel 25 detects the summation of the dispersed beam of light 13 for each of the different wavelengths $\lambda_1$ to $\lambda_n$ for the area covered by the pixel 25.

As the different wavelengths $\lambda_1$ to $\lambda_n$ in the dispersed beam of light 13 are shifted by different amounts the different wavelengths $\lambda_1$ to $\lambda_n$ that are incident on a given pixel of the detector 7 have passed though different portions of the modulator 3. This means that the different wavelengths $\lambda_1$ to $\lambda_n$ that are incident on a given pixel 25 of the detector 7 may be modulated by different amounts.

In the above examples the input beam of light 9 can be represented as $N_\lambda$ wavelength channels. Each of the wavelength channels has a spatial size $N_x \times N_y$.

The measurement Z obtained by the $(i,j)^{th}$ pixel where $Z \in \mathbb{R}^{N_x \times N_y}$ is given by equation 1

$$z(i,j) = \Sigma_{n_\lambda = 1}^{N_\lambda} S_0(i,j,n_\lambda) M(i,j,n_\lambda). \quad (1)$$

Where $S_0(i,j,n_\lambda)$ is the three dimensional input signal and $M(i,j,n_\lambda)$ is a function representing the modulator 3 and the dispersing element 5. The function $M(i,j,n_\lambda)$ will be dependent on the transparencies of the portions on the modulator 3, the spatial arrangement of the portions of the modulator 3, the dispersing element 5 and any other suitable factors.

The modulator 3 may be represented as a matrix $\{M^{(n_\lambda)}\}_{N_\lambda = 1}^{N_\lambda} \in \mathbb{R}^{N_x \times N_y}$. This allows the measurement Z obtained by each pixel 25 to be written in matrix form as $$z = Hs, \quad (2)$$

where z is a vectorized version of the measurement obtained by each pixel 25, s is the stacked vector of the three dimensional input beam of light $S_0(x,y,\lambda)$ and $H \in \mathbb{R}^{(N_x N_y) \times (N_x N_y N_\lambda)}$ is the sensing matrix and can be represented by equation 3.

$$H = [\text{Diag}(M^{(1)}), \ldots \text{Diag}(M^{(N_\lambda)})] \quad (3)$$

In examples of the disclosure s is the spectral domain signal provided by an OCT arrangement. This allows equation (2) to be rewritten as $$z = HFx \quad (4)$$

Where $x \in \mathbb{R}^{N_x N_y N_\lambda}$ denote the three dimensional image of the object and F is the Fourier transform $F \in \mathbb{R}^{(N_x N_y N_\lambda) \times (N_x N_y N_\lambda)}$. The image can therefore be obtained by solving $$x = \underset{x}{\text{argmin}} \|z - HFx\|^2 + \tau R(x) \quad (5)$$

where R(x) denotes the regularizer imposed on the OCT image x, and $\tau$ balances the two terms in equations (5). Any suitable compressive sensing inversion algorithms may be used to solve equation (5) to obtain the desired image.

Figure 3:
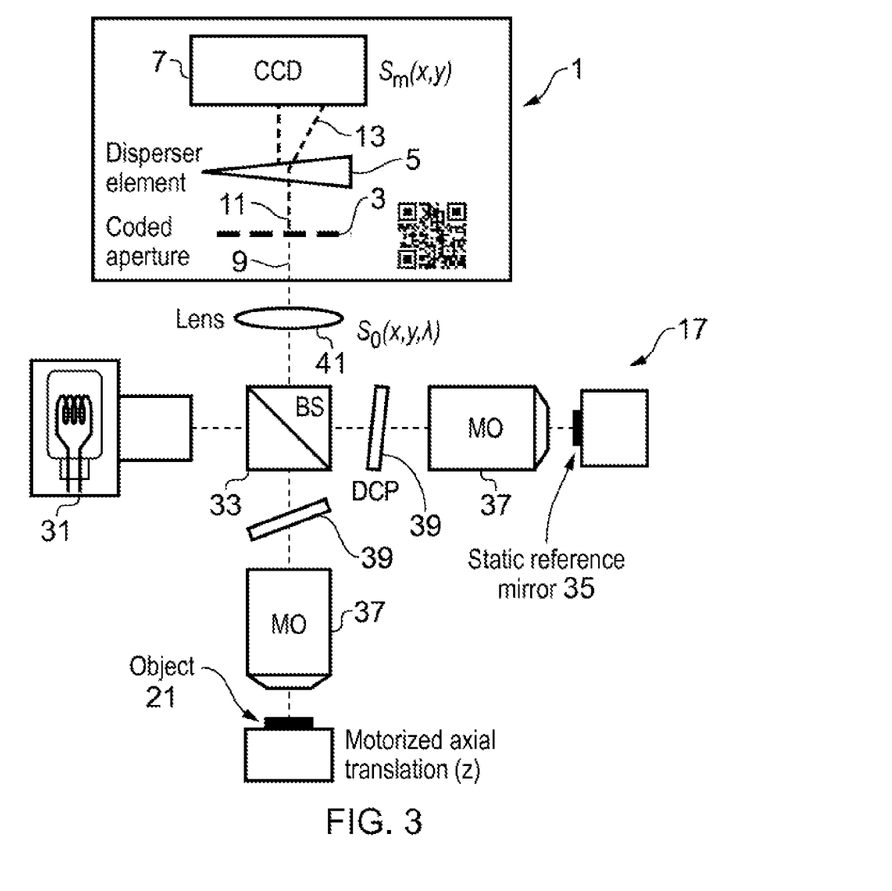
FIG. 3 illustrates an optical coherence tomography arrangement and an apparatus.

FIG. 3 illustrates an optical coherence tomography arrangement 17 and an apparatus 1 according to examples of the disclosure.

The OCT Arrangement comprises a light source 31, a beam splitter 33, a static reference mirror 35, one or more microscope objectives 37, one or more compensators 39, and one or more focusing elements 41. The OCT arrangement 17 is a spectral domain arrangement.

In examples of the disclosure the light source 31 is a broad beam light source which provides light having a range of wavelengths. The wavelength of the light that is used may depend on the type of object 21 that is to be imaged or any other suitable factor. In some examples the light used may be infrared light. in some examples the wavelength of the light used may be between 400 nm to 1500 nm.

The output light beam from the light source 31 is incident on the beam splitter 33. The beam splitter 33 may comprise a prism, a half silvered mirror or any other suitable component.

In the OCT arrangement 17 half of the split beam provides the reference beam and is provided to the static reference mirror 33. A microscope objective 37 and a compensator 39 are provided between the beam splitter 33 and the static reference mirror 35. The microscope objective 37 may comprise any means which may be arranged to focus the beam of light. In some examples the microscope objective 37 may comprise one or more lenses or any other suitable optical elements. The compensator 39 may comprise a compensator plate or any other suitable compensating element. In the example of FIG. 3 the compensator 39 comprises a decoupling compensator polarizer.

The other half of the split beam provides the object beam and is provided to the object 21. The object 21 may be arranged to be moved along the z axis. This axis may enable the focusing of the images provided by the OCT arrangement 17. In the example of FIG. 3 the object 21 is provided on a motorized arrangement so as to enable movement along the z axis. In other examples a manual arrangement, or any other suitable type of arrangement, could be used.

A microscope objective 37 and a compensator 39 are provided between the beam splitter 33 and the object 21. The microscope objective 37 may comprise any means which may be arranged to focus the beam of light. In some examples the microscope objective 37 may comprise one or more lenses or any other suitable optical elements. The compensator 39 may comprise a compensator plate or any other suitable compensating element. In the example of FIG. 3 the compensator 39 comprises a decoupling compensator polarizer.

The different frequencies of the light provide coherence of the object beam and the reference beam at different optical path lengths. Therefore the different frequencies of light provide information about different depths within the object 21. Different features within the object 21 reflect the incident light by different amounts. The interference between the reflected object beam and the reflected reference beam therefore provides information about the features within the object.

As the different frequencies of light provide information about different depths within the object 21 this enables three dimensional imaging of the object 21. The three dimensional imaging 21 may enable different features at different depths within the object to be identified and/or analysed. This ensures that the information obtained in the examples of the disclosure comprises information about the internal structure of an object 21 and not just information about the surface of the object 21.

The OCT arrangement 17 also comprises one or more focusing elements 41. The focusing element 41 may comprise a lens or any other suitable means for focusing a beam of light. The focusing element 41 is arranged to focus the beam of light into the apparatus 1 for detecting.

In the example of FIG. 3 the apparatus 1 comprises a modulator 3, a disperser element 5 and a detector 7.

The input beam of light 9 provided to the apparatus 1 from the OCT arrangement 17 is a three dimensional signal which may be represented as $S_0(x,y,\lambda)$, where $(x,y)$ are the two dimensional spatial axes and $\lambda$ denotes the wavelength of the light.

The signal that is detected by the detector 7 may be represented as $S_m(x,y)$ where:

$$S_m(x,y) = \int_\lambda S_0(x,y,\lambda) M(x,y,\lambda) d\lambda. \quad (6)$$

In equation (6) $M(x,y,\lambda)$ represents the modulation by the modulator 3 given by $M^*(x,y)$ and also the displacement by the disperser element 5 such that:

$$M(x, y+d(\lambda_n-\lambda_c), \lambda_n) = M^*(x,y) \quad (7)$$

where $\lambda_n$ is wavelength of $n^{th}$ channel and $\lambda_c$ is the center-wavelength, $d(\lambda_n-\lambda_c)$ signifies the spatial shifting of the mask for $n^{th}$ channel.

In the example of FIG. 3 a single pixel 25 in the detector 7 will detect multiple wavelengths of light. For each pixel 25 the measurement is given by $$z(i,j) = \Sigma_{n_\lambda=1}^{N_\lambda} S_0(i,j,n_\lambda) M(i,j,n_\lambda). \quad (8)$$

Therefore the apparatus 1 enables the three dimensional input signal to be mapped to a two dimensional signal which can then be detected by a detector 7 such as a charge-coupled device. The detector 7 can detect the different wavelengths simultaneously so that all the information is obtained in a single image. The apparatus 1 therefore enables $N_\lambda$ channel signals to be recovered from a single measurement.

Figure 4:
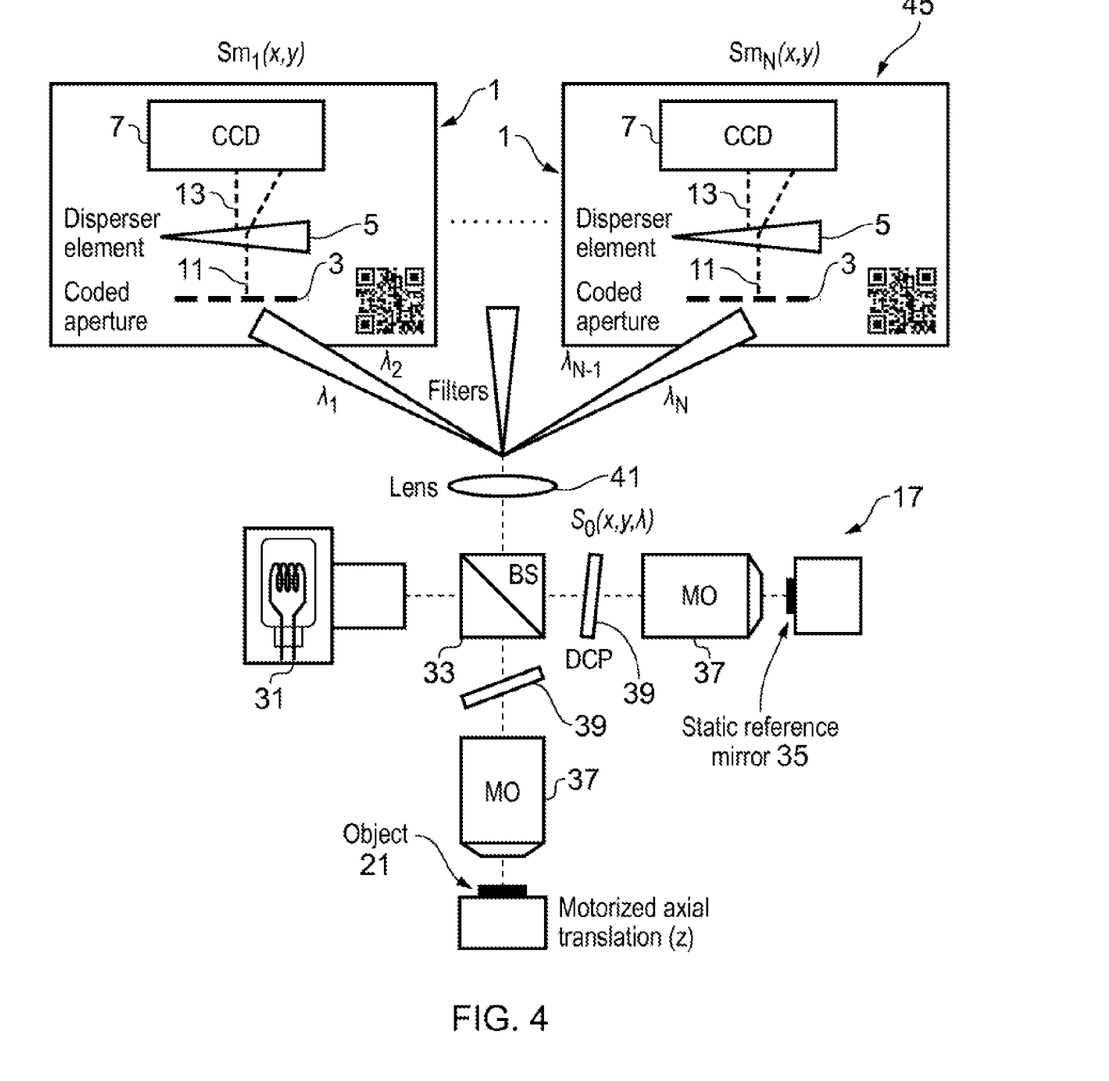
FIG. 4 illustrates an optical coherence tomography arrangement and a system comprising a plurality of apparatus.

FIG. 4 illustrates an OCT arrangement 17 and a system 45 comprising a plurality of apparatus 1. The OCT arrangement 17 may be as described above in relation to FIG. 3.

Each of the apparatus 1 may be as described above. Each of the apparatus 1 may be arranged to detect a different bandwidth of the light provided by the OCT arrangement 17. The system 45 comprises a plurality of filters 47. The filters 47 are arranged to provide different bandwidths of light to the different apparatus 1. This enables the different apparatus 1 to detect the different bandwidths simultaneously.

In the example system 45 of FIG. 4 each of the modulators 3 and the disperser elements 5 in the different apparatus 1 may be identical however each filter 47 is different to enable different bandwidths of light to be provided to the different apparatus 1. In other examples some of the modulators 3 and/or the disperser elements 5 could be different.

In the example of FIG. 4 the system 45 comprises N apparatus 1 and each apparatus 1 detects part of the signal $S_0(x,y,\lambda)$. The measurements that are obtained simultaneously are given by:

$$S_{m_1}(x,y) = \int_{\lambda_1}^{\lambda_2} S_0(x,y,\lambda) M(x,y,\lambda) d\lambda.$$

$$S_{m_2}(x,y) = \int_{\lambda_2}^{\lambda_3} S_0(x,y,\lambda) M(x,y,\lambda) d\lambda.$$

$$\vdots$$

$$S_{m_N}(x,y) = \int_{\lambda_{N-1}}^{\lambda_N} S_0(x,y,\lambda) M(x,y,\lambda) d\lambda.$$

As the different apparatus 1 within the system 45 each detect part of signal $S_0(x,y,\lambda)$ this enables more information to be obtained from each pixel 25 compared to the example of FIG. 3. Furthermore the example system 45 of FIG. 4 enables the different parts of the signal $S_0(x,y,\lambda)$ to be detected simultaneously. This therefore provides for a fast method of obtaining the information from the OCT arrangement 17.

Figure 5:
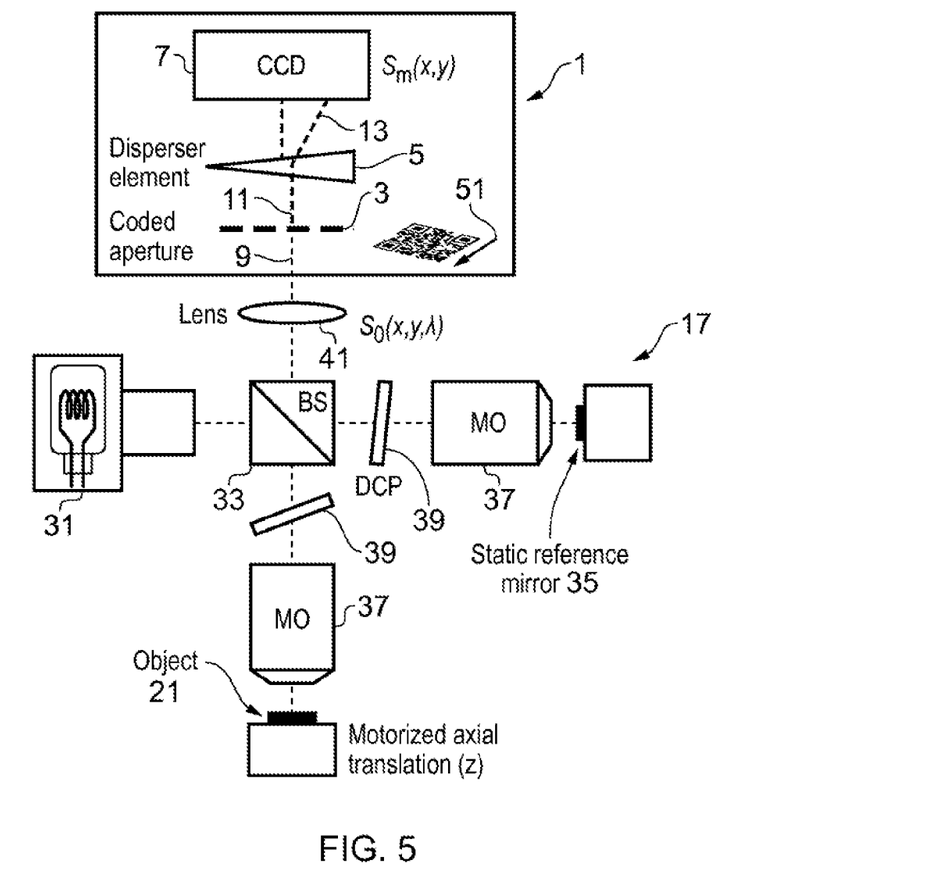
FIG. 5 illustrates an optical coherence tomography arrangement and an apparatus.

FIG. 5 illustrates an OCT arrangement 17 and coupled to another apparatus 1. The example apparatus 1 of FIG. 5 may be used to obtain OCT measurements sequentially. The OCT arrangement 17 may be as shown in FIGS. 3 and 4. The apparatus 1 may comprise a disperser element 5 and a detector 7 as described above.

The apparatus 1 also comprises a modulator 3 the modulator 3 may comprise a coded aperture or any other suitable means as described above. In the example of FIG. 5 the modulator 3 is arranged to be moveable relative to the other components of the apparatus 1. In the example of FIG. 5 the modulator 3 is arranged to be moveable relative to the disperser element 5 and the detector 7. In the example of FIG. 5 the modulator 3 is arranged to move as indicated by the arrow 51. In other examples the modulator 3 may be arranged to be moved in other directions. The modulator 3 may be arranged to move in any direction which is different to the direction in which the dispersing element 5 disperses the modulated beam of light 11.

Any suitable means may be provided to enable the modulator 3 to be moved. In some examples the modulator 3 may be moved by a motor, a piezo electric stage or any other suitable means. The modulator 3 is arranged to be moved during the time period between different measurements.

The modulator 3 is arranged to be moved in a direction which is different to the direction in which the light is dispersed by the dispersing element 5. In some examples the modulator 3 may be arranged to be moved in a direction perpendicular, or at least substantially perpendicular, to the direction in which the light is dispersed by the dispersing element 5. For example, the disperser element 5 may disperse the light towards an x direction so the modulator 3 may be arranged to move in a y direction. It is to be appreciated that the modulator 3 could be moved in other directions in other examples of the disclosure.

In the example of FIG. 5 N different measurements may be obtained. The modulator 3 used for each measurement is a shifted version of the same modulator 3. The N different measurements are therefore given by:

$$S_{m_1}(x, y) = \int_\lambda S_0(x, y, \lambda) M_1(x, y, \lambda) d\lambda.$$

$$S_{m_2}(x, y) = \int_\lambda S_0(x, y, \lambda) M_2(x, y, \lambda) d\lambda$$

$$\vdots$$

$$S_{m_N}(x, y) = \int_\lambda^\lambda S_0(x, y, \lambda) M_N(x, y, \lambda) d\lambda$$

These can then be solved for $S_0(x,y,\lambda)$ given the shifted modulators $\{M_n(x,y,\lambda)\}_{n=1}^N$ Having multiple measurements being obtained sequentially may enable more information to be obtained than from one single measurement as obtained by the example apparatus 1 of FIG. 1.

Figure 6:
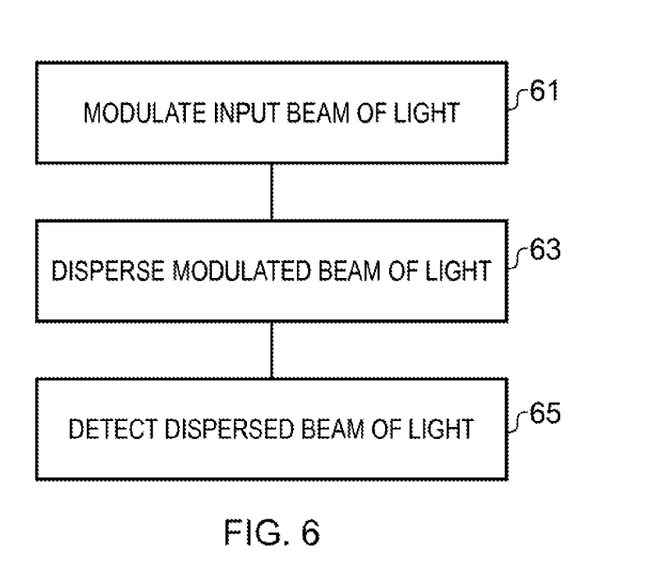
FIG. 6 illustrates a method.

FIG. 6 illustrates an example method. The method may be implemented using any of the example apparatus 1 and systems 45 described above.

At block 61 the method comprises modulating an input beam of light 9. The input beam of light 9 is obtained from an OCT arrangement 17. At block 63 the method comprises dispersing the modulated beam of light 11 and, at block 65 the method comprises detecting the dispersed beam of light 13 and converting the detected beam of light into an electrical output signal.

It is to be appreciated that in some examples the method may comprise further blocks that are not shown in FIG. 6. For instance, in some examples a modulator 3 such as a coded aperture may be used to modulate the input beam of light 9 and the method may comprise moving the modulator 3 so that different bandwidths are detected sequentially.

Figure 7:
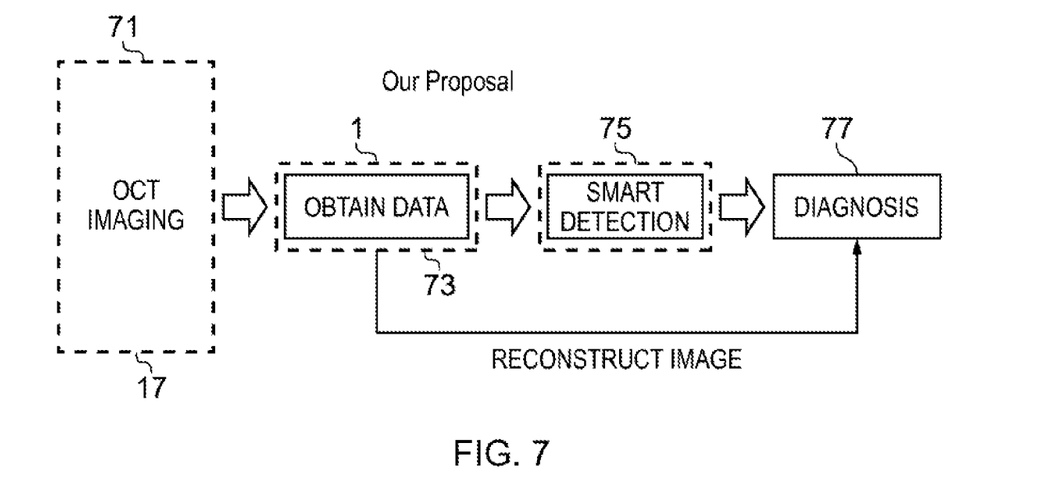
FIG. 7 illustrates a method of using examples of the disclosure.

FIG. 7 illustrates a method of using examples of the disclosure which may be used to enable a medical diagnosis. At block 71 the OCT imaging is performed. The object 21 that is imaged may the retina of a person or animal or any other suitable object 21. The OCT imaging is performed by an OCT arrangement 17 which may be as described above.

At block 73 the data from the OCT imaging is obtained. The data is obtained by an apparatus 1 or plurality of apparatus 1 as described above. The data obtained by the apparatus 1 or plurality of apparatus 1 is modulated by the modulator 3. This enables the data to be captured in a compressed manner. This may provide for an efficient use of memory circuitry and communication bandwidths.

The obtained data is detected by the one or more detectors 7 as described above. The electrical output of the one or more detectors 7 may be used, at block 75 for smart detection. The smart detection may comprise the use of algorithms, or any other suitable technique, to recognize features in the output signal of the detectors 7. This information could then be provided to the user, who may be a medical professional, at block 77. The information that is provided may be used to enable a diagnosis by the medical professional.

In some examples, at block 77, the output signal from the detector 7 may be used to reconstruct an image of the object 21, or at least part of the object 21. This may also be provided to the medical professional to assist with any diagnosis.

The described examples therefore provide a low cost compressive detecting apparatus 1 for a spectral OCT arrangement 17. The example apparatus 1 provide for a fast capture of the information while providing for efficient use of communications bandwidths and memory circuitry.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . ." or by using "consisting".

In this brief description, reference has been made to various examples. The description of features or functions in relation to an example indicates that those features or functions are present in that example. The use of the term 'example' or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

I claim:

1. A method for obtaining a three dimensional image corresponding to at least a three-dimensional part of an object, the method comprising:

spatially modulating, using at least a modulator, an input beam of light, wherein the input beam of light is a spectral domain signal obtained from an optical coherence tomography arrangement and comprises light reflected from the object that comprises different frequencies of light providing information about different depths within the object, and wherein the modulator comprises at least a first plurality of first portions having a first transparency to the input beam of light and at least a second plurality of second portions having a different transparency to the input beam of light, the first and second portions of the modulator being arranged in a pixelated arrangement;

dispersing the modulated beam of light;

detecting the dispersed beam of light as a single measurement;

converting the detected beam of light into electrical output signals; and providing the three dimensional image of at least the three-dimensional part of the object from the electrical output signals.

2. The method of claim 1, wherein the modulator comprises a coded aperture.

3. The method of claim 2, further comprising:
using the coded aperture to modulate the beam of light and moving the coded aperture so that different spectral bandwidths are detected sequentially.

4. The method of claim 2, wherein the coded aperture is a two dimensional coded aperture.

5. The method of claim 1, wherein the transparency of the first and second portions of the modulator are wavelength dependent.

6. The method of claim 1, wherein the first and second portions of the modulator are arranged in a random or pseudo random pattern.

7. The method of claim 1, wherein the modulator is arranged to convert a three dimensional signal into a two dimensional signal.

8. The method of claim 1, wherein providing the three dimensional image of at least the three-dimensional part of the object from the electrical output signals uses a compressive sensing inversion algorithm that converts candidate three dimensional images into the spectral domain using a Fourier transform.

9. An apparatus for obtaining a three dimensional image corresponding to at least a three-dimensional part of an object, the apparatus comprising:
a modulator configured to spatially modulate an input beam of light, wherein the input beam of light is a spectral domain signal obtained from an optical coherence tomography arrangement and comprises light reflected from an object that comprises different frequencies of light providing information about different depths within the object, and wherein the modulator comprises at least a first plurality of first portions having a first transparency to the input beam of light and at least a second plurality of second portions having a different transparency to the input beam of light, the first and second portions of the modulator are arranged in a pixelated arrangement;
a dispersing element configured to disperse the modulated beam of light; and
a detector configured to detect the dispersed beam of light as a single measurement and convert the detected beam of light into electrical output signals, wherein the apparatus is configured to provide a three dimensional image of at least the three-dimensional part of the object based at least upon the electrical output signals.

10. The apparatus of claim 9, wherein the modulator comprises a coded aperture, the modulator being configured to modulate the beam of light and move the coded aperture so that different spectral bandwidths are detected sequentially.

11. The apparatus of claim 10, wherein the coded aperture is a two dimensional coded aperture.

12. The apparatus of claim 9, wherein the modulator is arranged to be moveable relative to the dispersing element and the detector.

13. The apparatus of claim 9, wherein the dispersing element comprises a prism.

14. The apparatus of claim 9, wherein the detector comprises at least one of a: charge coupled device or a complementary metal-oxide semiconductor sensor.

15. The apparatus of claim 9, wherein the detector comprises a two dimensional array of sensors.

16. The apparatus of claim 9, wherein the first and second portions of the modulator correspond to pixels in the detector.

17. The apparatus of claim 9, wherein the transparency of the first and second portions of the modulator are wavelength dependent.

18. The apparatus of claim 9, wherein the first and second portions of the modulator are arranged in a random or pseudo random pattern.

19. The apparatus of claim 9, wherein the modulator is configured to convert a three dimensional signal into a two dimensional signal.

20. The apparatus of claim 9, wherein the apparatus is configured to provide the three dimensional image of at least the three-dimensional part of the object from the electrical output signals using a compressive sensing inversion algorithm that converts candidate three dimensional images into the spectral domain using a Fourier transform.

21. A sensing system comprising:
a plurality of apparatuses, where respective apparatuses of the plurality of apparatuses comprise a modulator configured to spatially modulate an input beam of light, wherein the input beam of light is a spectral domain signal obtained from an optical coherence tomography arrangement and comprises light reflected from an object that comprises different frequencies of light providing information about different depths within the object, wherein the modulator comprises at least a first plurality of first portions having a first transparency to the input beam of light and at least a second plurality of second portions having a different transparency to the input beam of light, wherein the first and second portions of the modulator are arranged in a pixelated arrangement, respective apparatuses of the plurality of apparatuses further comprising a dispersing element configured to disperse the modulated beam of light and a detector configured to detect the dispersed beam of light as a single measurement and convert the detected beam of light into electrical output signals; and
one or more filters arranged to divide the input beam of light into a plurality of different spectral bandwidths, wherein the sensing system is arranged so that input beams of light of different bandwidths are provided to different apparatuses of the plurality of apparatuses.

22. The sensing system of claim 21, wherein respective apparatuses of the plurality of apparatuses are configured to provide the three dimensional image of at least the three-dimensional part of the object from the electrical output signals using a compressive sensing inversion algorithm that converts candidate three dimensional images into the spectral domain using a Fourier transform.

* * * * *